(12) United States Patent
Ko

(10) Patent No.: US 8,802,163 B2
(45) Date of Patent: Aug. 12, 2014

(54) NATURAL SOAP USING HERBAL MEDICINE MATURE DECOCTION, AND METHOD OF PREPARING THE SAME

(71) Applicant: Eun Joo Ko, Seoul (KR)

(72) Inventor: Eun Joo Ko, Seoul (KR)

( * ) Notice: Subject to any disclaimer, the term of this patent is extended or adjusted under 35 U.S.C. 154(b) by 0 days.

(21) Appl. No.: 13/735,397

(22) Filed: Jan. 7, 2013

(65) Prior Publication Data

US 2013/0196004 A1 Aug. 1, 2013

(30) Foreign Application Priority Data

Jan. 5, 2012 (KR) .................. 10-2012-0001442

(51) Int. Cl.
*A61K 36/258* (2006.01)

(52) U.S. Cl.
USPC ........... 424/728; 424/729; 424/732; 424/770; 424/747; 424/771; 424/756; 424/765; 424/744; 424/401

(58) Field of Classification Search
CPC ... A61K 8/97; A61K 36/258; A61K 36/9068; A61K 36/53; A61K 36/886; A61K 36/605; A61K 36/232; A61K 36/82; A61K 36/15; A61K 36/44; A61K 36/534; A61K 36/45; A61K 36/882
USPC ......... 424/732, 770, 747, 728, 771, 756, 765, 424/744, 729

See application file for complete search history.

(56) References Cited

U.S. PATENT DOCUMENTS

2011/0052731 A1 * 3/2011 Park et al. .................. 424/728

* cited by examiner

*Primary Examiner* — Susan Hoffman
(74) *Attorney, Agent, or Firm* — Sherr & Jiang, PLLC

(57) ABSTRACT

A natural soap is made using a herbal medicine decoction. The natural soap includes herbs including lotus roots, lotus leaves, red ginseng, *Hippophae rhamnoides* leaves and trunk, persimmon leaves, *thuja orientalis*, ginger, rosemary, black beans, black sesame, aloe, mulberry leaves, *Orostachys japonicus, Angelica gigas*, green tea, pine needles, mint, *pleuropterus multiflorus*, blueberry, and *Acorus gramineus*. A ripening device ripens the herbs in temperatures of 65 to 95° C. for 3 to 15 days, distilled water or soft water is poured onto the herbs, and the herbs mixed with the water are decocted by a decoction maker.

5 Claims, 2 Drawing Sheets

FIG.2

After Use Evaluation Questionnaire

Product name: NATURAL SOAP BY USING OF RIPEN AND DECOCTED ORIENTAL MEDICINE

<Evaluation Table>

Genter: M / F     Age:_____

| Evaluation Item | Very Good (5) | Good (4) | Not Bad (3) | Bad (2) | Very Bad (1) |
|---|---|---|---|---|---|
| Hair Loss Prevention | | | | | |
| Hair Growth Stimulation | | | | | |
| Soap Bubbles | | | | | |
| Detergency | | | | | |
| Fragrance | | | | | |
| Moisturizing Effect | | | | | |
| Comment | | | | | |

…

NATURAL SOAP USING HERBAL MEDICINE MATURE DECOCTION, AND METHOD OF PREPARING THE SAME

CROSS-REFERENCE TO RELATED PATENT APPLICATION

This application claims the benefit of Korean Patent Application No. 10-2012-0001442, filed on Jan. 5, 2012, in the Korean Intellectual Property Office, the disclosure of which is incorporated herein in its entirety by reference.

BACKGROUND OF THE INVENTION

1. Field of the Invention

The present invention relates to a natural soap prepared by using a herbal medicine mature decoction made by maturing a herbal medicine at a high temperature and decocting the matured herbal medicine, and more particularly, to a natural soap using a herbal medicine mature decoction which may be easy to be used by significantly reducing unpleasant smell of natural herbs, may be mixed with various natural herbs by reducing the attribute of the natural herbs of being separated from an carrier oil, may be stored for a long time by doubling elements having medical effects of natural herbs, may prevent loss of hair and stimulate hair growth by improving detergency using grain powder without using a synthetic surfactant, and a method of preparing the same.

2. Description of the Related Art

Generally, a natural soap is a soap prepared without a synthetic surfactant and by adding a functional element such as a natural element and aroma oil in a home or in a small scale, which is contrasted with soaps manufactured in a large scale in a factory in a current situation in which environmental friendliness and well-being are emphasized and harmfulness of the synthetic surfactant is being highlighted.

The natural soap may be broadly divided into a melt & pour (MP) soap, a hot process (HP) soap, and a cold process (CP) soap depending on the manufacturing method.

In order to make the MP soap, a soap base is melt, and the melt soap base is poured in a mold along with additives, and then hardened. The soap has a good detergency, and is promptly available, but because there are not sufficient moisturizing elements, and thus glycerin, collagen, honey, etc. should be added. The HP soap is also called a transparent soap or glycerin soap. This soap is made by mixing caustic soda with oil in a high temperature. The soap has a good detergency, and the fragrance lasts for a long time. In order to make the HP soap, the elements should be heated in a water bath for 2 to 3 hours, or directly heated for 40 to 50 minutes, and thereafter, the heated elements should be matured in a normal temperature for 2 weeks. The CP soap is made by reacting caustic soda with oil in a low temperature and adding several additives. The CP soap is opaque, and a 6 week maturing period in a normal temperature is needed.

Such a natural soap does not contain synthetic perfume and artificial colorants, and moisturizing effects are good and harmfulness is less. However, the natural soap is not hard, and thus is easily softened and broken.

Further, the expiration date of the natural soap is only 6 months from the manufacturing date because preservatives are not added.

Further, recently, in order to add functionality to natural soaps, some herbal medicine powders have been added to the soaps.

The present applicant has also performed a lot of experiments for several years with an intention to add boiled or decocted herbal medicine to a natural soap because boiled or decocted herbal medicine is significantly more effective than powder, but many herbs except only a few herbs have not been mixed with carrier oil, the essential element for the natural soap, and thus the soap has not been made.

Therefore, it has been substantially impossible to make a natural soap which contains boiled or decocted herb medicines.

SUMMARY OF THE INVENTION

The present invention provides a natural soap using a herbal medicine mature decoction which may be easy to be used by significantly reducing unpleasant smell of natural herbs, may be mixed with various natural herbs by reducing the attribute of the natural herbs of being separated from an carrier oil, may be stored for a long time by doubling elements having medical effects of natural herbs, may prevent loss of hair and stimulate hair growth by improving detergency using grain powder without using a synthetic surfactant, and a method of preparing the same.

According to an aspect of the present invention, there is provided a natural soap made using a herbal medicine mature decoction which is obtained by putting herbs including lotus roots, lotus leaves, red ginseng, *Hippophae rhamnoides* leaves and trunk, persimmon leaves, *thuja orientalis*, ginger, rosemary, black beans, black sesame, aloe, mulberry leaves, *Orostachys japonicus*, *Angelica gigas*, green tea, pine needles, mint, *pleuropterus multiflorus*, blueberry, and *Acorus gramineus* in a maturing device, maturing the herbs in temperatures of 65 to 95° C. depending on the herb for 3 to 15 days, then pouring distilled water or soft water, and decocting the matured herbs mixed with the water.

The herbal medicine mature decoction may be obtained by putting the herbs matured in the temperatures along with the distilled water or soft water in a decoction maker, then boiling the herbs mixed with the water by strong heat, then decocting the herbs mixed with the water by weak heat so as to make a first decoction, then pouring the first decoction in another vessel, then pouring distilled water or soft water in the decoction maker, then boiling the herbs mixed with the water by strong heat, then decoct the herbs mixed with the water by weak heat so as to make a second decoction, then removing the herbs from the second decoction, then mixing the first decoction with the second decoction, and then decocting the mixed decoction by weak heat.

According to another aspect of the present invention, there is provided a method of preparing a natural soap by adding a caustic soda, including: washing herbs including 6 to 9 weight % of lotus roots, 4 to 6 weight % of lotus leaves, 4 to 6 weight % of red ginseng, 4 to 6 weight % of *Hippophae rhamnoides* leaves and trunk, 4 to 6 weight % of persimmon leaves, 4 to 6 weight % of *thuja orientalis*, 4 to 6 weight % of ginger, 3 to 5 weight % of rosemary, 6 to 9 weight % of black beans, 3 to 5 weight % of black sesame, 5 to 8 weight % of aloe, 5 to 8 weight % of mulberry leaves, 1 to 3 weight % of *Orostachys japonicus*, 4 to 6 weight % of *Angelica gigas*, 3 to 5 weight % of green tea, 5 to 8 weight % of pine needles, 4 to 6 weight % of mint, 4 to 6 weight % of *pleuropterus multiflorus*, 3 to 5 weight % of blueberry, and 3 to 5 weight % of *Acorus gramineus*, putting the washed herbs in a maturing device, and maturing the herbs at temperatures of 65 to 95° C. for 3 to 15 days depending on the herb (S100); putting the matured herbs along with 15 to 25 weight % of distilled water and 75 to 85 weight % of soft water in a decoction maker, boiling the herbs mixed with the water by strong heat, and decocting the herbs mixed with the water by weak heat for 48 to 72 hours so as to make a first decoction (S200); pouring the first decoction into a vessel, putting 37 to 43 weight % of distilled water or soft water in the decoction maker, boiling the herbs mixed with the water by strong heat and decocting the herbs mixed with the water by weak heat for 3 to 4 hours so as to make a second decoction (S300); removing the herbs from the decoction maker, mixing the first decoction with the second decoction, and decocting the mixed decoction for 24 to 36 hours by weak heat so as to obtain a herbal medicine mature decoction of 7.5 to 8.5 weight % (S400); mixing 65 to 75 weight % of the herbal medicine mature decoction with 25 to 35 weight % of the caustic soda, and cooling the mixture down to a temperature of 40 to 55° C. (S500); heating 65 to 75 weight % of carrier oil, which is a mixture of at least two of coconut oil, palm oil, olive oil, camellia oil, castor oil, rice bran oil, sunflower oil, and grape seed oil, to 40 to 55° C., and slowly pouring 25 to 35 weight % of the cooled mixture of the caustic soda and the herbal medicine mature decoction into the heated carrier oil and stirring the mixture at the same time so as to form a soap (S600); adding 2 to 5 weight % of essential oil, which is a mixture of at least two of lavender, lemon, clary sage, ylang ylang, rosemary, tea tree, and cedarwood, to the 95 to 98 weight % of the saponified mixture, and stirring the mixture (S700); pouring the mixture including the essential oil into a mould, and maturing the mixture at a temperature of 30 to 40° C. for 48 to 72 hours (S800); and separating the solid soap from the mould after the maturing of the mixture, and maturing the soap in a shady and drafty area in a room temperature of 22 to 28° C. for 4 to 6 weeks (S900).

The method may further include at least one of: adding 5 to 10% of the functional powder including at least one of black sesame powder, black rice powder, black bean powder, chlorella powder, and Japanese cypress leaf powder to 90 to 95 weight % of the saponified mixture, and stirring the mixture (S650); and adding 1 to 15 weight % of fragments of a natural soap produced before to the 85 to 99% of the mixture including the essential oil (S750).

According to the present invention, there are effects of providing a natural soap using a herbal medicine mature decoction which may be easy to be used by significantly reducing unpleasant smell of natural herbs, may be mixed with various natural herbs by reducing the attribute of the natural herbs of being separated from an carrier oil, may be stored for a long time by doubling elements having medical effects of natural herbs, may prevent loss of hair and stimulate hair growth by improving detergency using grain powder without using a synthetic surfactant, and a method of preparing the same.

BRIEF DESCRIPTION OF THE DRAWINGS

The above and other features and advantages of the present invention will become more apparent by describing in detail exemplary embodiments thereof with reference to the attached drawings in which:

FIG. 2 is a questionnaire for checking the effects of a natural soap according to the present invention.

DETAILED DESCRIPTION OF THE INVENTION

Figure 1:
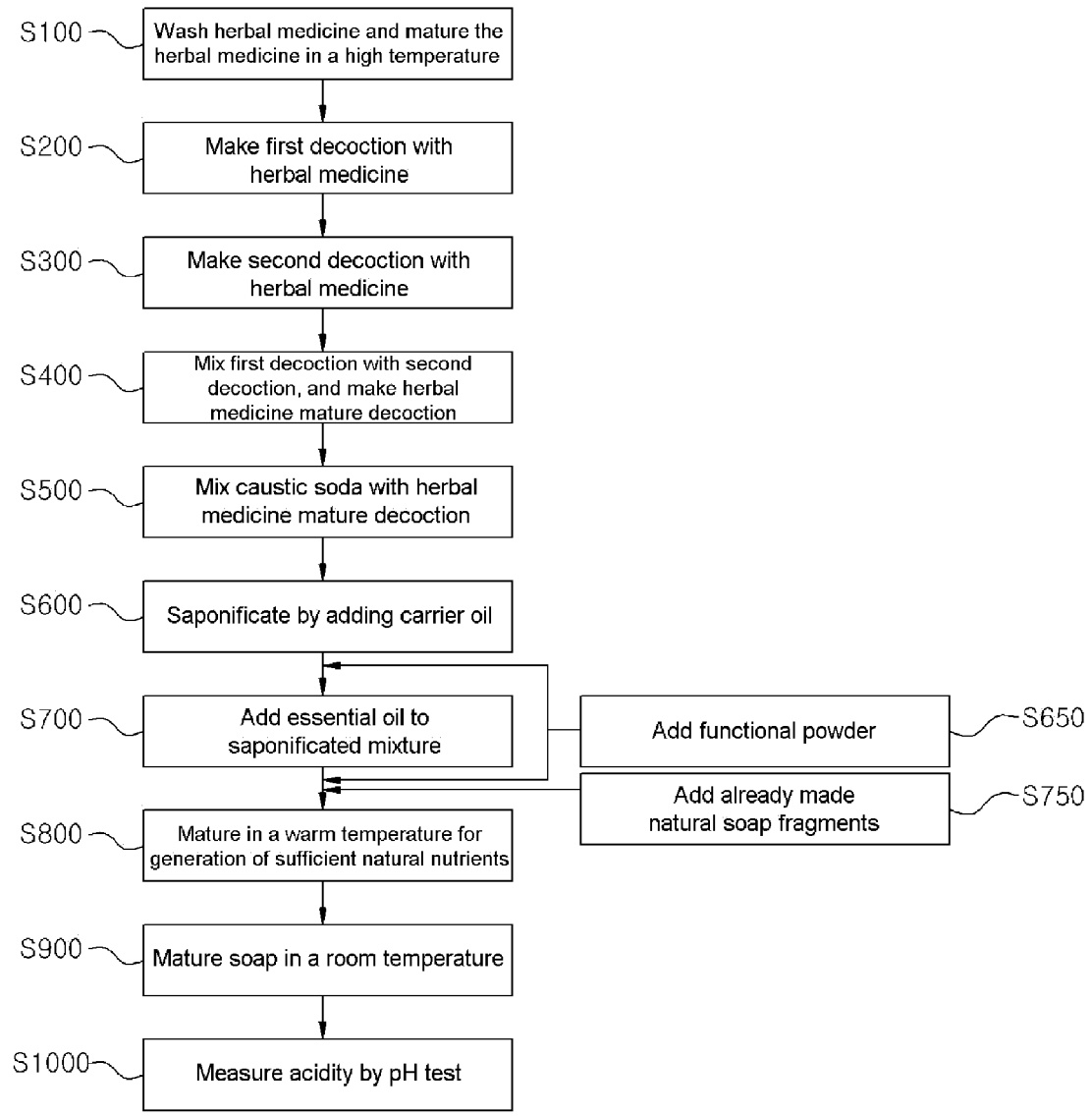
FIG. 1 is a process diagram illustrating a method of preparing a natural soap according to the present invention.

Exemplary embodiments of the present invention are described with reference to the accompanying drawings in detail. The same reference numbers are used throughout the drawings to refer to the same or like parts. Detailed descriptions of well-known functions and structures incorporated herein may be omitted to avoid obscuring the subject matter of the present invention.

Exemplary Embodiment 1

First, step 1 (S100) to step 4 (S400) are the process of making a herbal medicine mature decoction by high temperature maturing, and step 5 (S500) to step 9 (S900) are the process of making a natural soap using the prepared herbal medicine mature decoction.

The features of the present invention are found in the process of making a herbal medicine mature decoction by high temperature maturing from step 1 (S100) to step 4 (S400).

Step 1 (S100): Washing Herb Medicines and Maturing them in a High Temperature

Herbs having excellent effects on prevention of hair loss or stimulation of hair growth are chosen, washed in water, and matured in a high temperature so that a natural soap has excellent effects on prevention of hair loss or stimulation of hair growth.

Herbs selected in the present invention are 6 to 9 weight % of lotus roots, 4 to 6 weight % of lotus leaves, 4 to 6 weight % of red ginseng, 4 to 6 weight % of *Hippophae rhamnoides* leaves and trunk, 4 to 6 weight % of persimmon leaves, 4 to 6 weight % of *thuja orientalis*, 4 to 6 weight % of ginger, 3 to 5 weight % of rosemary, 6 to 9 weight % of black beans, 3 to 5 weight % of black sesame, 5 to 8 weight % of aloe, 5 to 8 weight % of mulberry leaves, 1 to 3 weight % of *Orostachys japonicus*, 4 to 6 weight % of *Angelica gigas*, 3 to 5 weight % of green tea, 5 to 8 weight % of pine needles, 4 to 6 weight % of mint, 4 to 6 weight % of *pleuropterus multiflorus*, 3 to 5 weight % of blueberry, and 3 to 5 weight % of *Acorus gramineus*. The selected herbs are washed in water, and are placed in a maturing device and are matured for 3 to 15 days at 65 to 95° C. depending on the material.

The maturing device is a device developed by the present applicant to mature herbs, and is a device which is shut tightly not to allow a leak of water of the herbs, and maintains the constant temperature.

The setting temperature of the maturing device is preferably between 80 and 90° C., and the maturing period is differentially about 3 to 15 days.

The present applicant has performed an experiment of maturing herbs in a high temperature based on the fact that the remedial effects significantly increase when ginseng is steamed at a high temperature without boiling it. Further, through the first step (S100) of maturing herbs at a high temperature, unpleasant smell of herbs is reduced, the remedial effects significantly increase, and the matured herbs may be stored for a long time and may be mixed well with each other and with carrier oil when making a decoction, thereby allowing production of soap. Hence, in the present invention, step 1 (S100) has most important technical features.

Among the herbal medicine, the lotus root has a lot of vitamin C protected by starch, and thus the vitamin C is not easily destroyed. As such, the lotus root has excellent effects of preventing pimples, freckles, and hair loss and promoting hair growth. Further, tannin helps blood circulation, and linolenic acid is a natural antioxidant and has effects of preventing aging. Further, mineral supplies nutrition to the scalp.

The remedial effects of the lotus leaves are similar to those of the lotus roots, but the lotus leaves especially have effects of quenching the thirst, soothing skin, reinforcing vigor, and detoxifying nicotine.

Red ginseng is a food for nutrition and robustness, and has a lot of effects such as fatigue recovery, immunity enhancement, platelet aggregation inhibition, hangover mitigation, aging prevention, high blood pressure and diabetes prevention, menopausal symptom improvement, and anemia prevention.

*Hippophae rhamnoides* leaves and trunk contain 15 kinds of vitamins, natural mineral, amino acids, saponin (4 times of ginseng), and have effects of treating high blood pressure, nervous prostration, heart disease, gestroenteric disorder, and eczema, and have anticancer effects, and effects of aging prevention and promotion of metabolism.

Persimmon leaves contains vitamin C (20 times of lemon), and has excellent effects on high blood pressure, scurvy, anemia, fatigue, and skin care.

*Thuja orientalis* remove unpleasant smell, make hair black, strengthen teeth and bones, have effects on treating or preventing hepatocirrhosis and liver cancer, and have effects on preventing high blood pressure and paralysis.

Ginger detoxifies the toxic elements of herbs and warms the body, and has effects of preventing hair loss and promoting hair growth.

Rosemary has excellent sterilizing power, has effects of aging prevention, calming effects, anti-oxidation effects, is used in a tea or a drink, and has effects of preventing hair loss and promoting hair growth.

Black beans normalize blood pressure, treats inflammation, and vitamin E, unsaturated fatty acids, anthocyanin, and beta carotene of the beans prevent aging. Further, estrogens, saponin, glycinin, etc. of the beans enlarge blood vessels, thereby relieving white hair and hair loss.

Black sesames contain unsaturated fatty acids which prevent hardening of the arteries, vitamin E and phospholipids which recover skin, and lecithin which is good to the brain, supplies nutrition to the scalp, thereby preventing hair loss and being helpful in anti-constipation.

Aloe improves fine wrinkles and scars, has antibiotic and anti-virus effects, cools the skin heat, relieves sensitive skin, has good moisturizing effects, heals and regenerates cells, washes, regenerates and moisturizes the scalp, and prevents hair loss.

Gava of mulberry leaves lowers blood pressure, strengthens the capillary vessel, thereby promoting hair growth, and has effects of preventing or healing apoplexy, high blood pressure, hardening of the arteries, and the heart disease.

*Orostachys japonicus* grows in an old roofing tile, and has excellent effects on cell activation, DNA immunity enhancement, detoxication, liver function recovery, and regeneration and recovery of damaged cells.

*Angelica gigas* improve the circulation of blood, strengthen the heart function, mitigates the cold symbols of hands and foot, prevents aging, improves the scalp condition and promotes hair growth.

Green teas contain a lot of catechin having strong anticancer effects, inhibits inflammation and germ infection, inhibits the rise of the blood sugar level, prevents aging, detoxifies nicotine and heavy metal, recovers hangover and fatigue, changes acidic constitution, removes carious teeth and bad breath, and improves the skin state.

Pine needles contain chlorophyll, vitamin A, and vitamin C, has curative effects on apoplexy, high blood pressure, hardening of the arteries, haemorrhoids, dermatitis, kidney disease, anemia, and neuralgia, and regenerates cells, prevents aging, prevents hair loss and promotes hair growth.

Mints contain a lot of manganese, vitamin A and vitamin C, and thus have antibiotic effects, cool the heat, removes the skin damage and inflammation, invigorates the person, relieves the itching, promotes the blood circulation, reduces pores, and has curative effects on pimples and dermatitis.

*Pleuropterus multiflorus* enlarges blood vessels, regenerates skin cells, and has effects on hair gloss, white hair prevention, hair loss prevention and hair growth promotion.

Blueberries are one of the world's top 10 health foods, and strengthens eyesight, ha anticancer effects, prevents aging, and has curative effects on constipation, osteoporosis, etc.

*Acorus gramineus* clears the head, improves memory, prevents aging, and makes hair glossy and maintains the health of hair.

Step 2 (S200): Making a First Decoction Using Herbal Medicines

Herbs, which have been matured in a high temperature, have significantly reduced unpleasant smell, and may now be mixed with each other, are put in a decoction maker along with 15 to 25 weight % of distilled water and 75 to 85 weight % of soft water, then they are boiled with strong heat, then they are boiled with weak heat for 48 to 72 hours so as to make the first decoction.

Water put in the decoction maker along with herbs should be distilled water and soft water, not tap water. The reason why distilled water and soft water should be used is because tap water contains materials which have been used at the time of chemical treatment and the materials lower the curative effects of the herbal medicines, and when the materials are reacted with caustic soda, unusual reaction occurs.

Step 3 (S300): Making a Second Decoction with Herbal Medicines

The first decoction made in step 2 (S200) is poured in another vessel, and 37 to 43 weight % of distilled water or soft ware is poured in the original vessel, then the water in the original vessel is boiled by strong heat, and is then boiled by weak heat for 3 to 4 hours so as to make the second decoction.

Step 4 (S400): Mixing the First Decoction with the Second Decoction and Boiling the Mixed Decoction to Make an Herbal Medicine Mature Decoction After removing the herbal medicines from the second decoction vessel, the first decoction is mixed with the second decoction, and then the mixed decoction is boiled with weak heat for 24 to 36 hours so as to obtain an herbal medicine mature decoction of 7.5 to 8.5 weight %.

Through the process of making the first decoction and the second decoction using the herbal medicines, and making the herbal medicine mature decoction by mixing the first decoction and the second decoction and boiling the mixed decoction, the herbal medicines, which have been matured in a high temperature, now have significantly less unpleasant smell and may be mixed with each other.

Step 5 (S500): Mixing the Herbal Medicine Mature Decoction with Caustic Soda 65 to 75 weight % of the herbal medicine mature decoction is mixed with 25 to 35 weight % of the caustic soda, and the mixture is cooled to 40 to 55° C.

No water is added when the herbal medicine mature decoction is mixed with the caustic soda. The caustic soda reacts with the herbal medicine mature decoction, and thereby emits gas and generates intense heat, and this is cooled down to 40 to 50° C.

Step 6 (S600): Adding Carrier Oil so as to Make Soap 65 to 75 weight % of carrier oil, which is a mixture of at least two of coconut oil, palm oil, olive oil, camellia oil, castor oil, rice bran oil, sunflower oil, and grape seed oil is heated to 40 to 55° C., and 25 to 35 weight % of the cooled mixture of the caustic soda and the herbal medicine mature decoction is slowly poured in the heated carried oil, and the mixture is stirred so as to form soap.

When the mixture of the caustic soda and the herbal medicine mature decoction is added to the carrier oil, the person in charge stirs them while slowly pouring the mixture in the carrier oil, and viscosity increases to the point when, if the final mixture is dropped, a mark remains. This point is called the trace state, and implies that soap has been formed well.

When all of the carrier oils are added, 25 to 35 weight % of coconut oil, 22 to 32 weight % of palm oil, 6 to 16 weight % of olive oil, 4 to 14% of camellia oil, 4 to 14 weight % of castor oil, 1 to 11 weight % of rice bran oil, 1 to 11 weight % of sunflower oil, and 0.5 to 9 weight % of grape seed oil may be used for 65 to 75 weight % of the carrier Oil.

Step 7 (S700): Adding Essential Oil to Saponificated Mixture 2 to 5 weight % of essential oil, which is the mixture of at least two of lavender, lemon, clary sage, ylang ylang, rosemary, tea tree, and cedarwood, is added to the 95 to 98 weight % of the saponificated mixture, and then stirred.

The essential oil is added because, even if most of unpleasant smell of natural herbs has been removed through the first decoction and the second decoction, but unique herbal medicine smell still remains. Hence, in order to remove the remaining smell and add functional features of each oil, the essential oil is added.

In the essential oil, lavender has strong fragrance and preservative effects, has curative effects on pimples, dermatitis, tumors, eczema, a bite by a bug, athlete's feet, ringworm, injury, and wrinkles, and has curative effects on stress, depression, insomnia, and headache.

Further, lemon helps fatigue recovery, blood circulation, metabolism activation, skin and mucous membrane reinforcement, and reinforcement of resistance to bacteria, and has effects on skin peeling of oily skin, injury recovery, and hair cleansing.

Further, clary sage has effects of preservation from decay, sterilization, tranquilization, prevention of unpleasant smell, and removal of fever, has effects on sensitive skin, stress, external wound, seborrheic dandruff, and promotes hair growth.

Further, ylang ylang has tranquilization effects, preservative effects, aphrodisiac effects, pimple treatment effects, normal blood pressure maintenance effects, pain killing effects, hair loss prevention effects, skin water balance regulation effects, and hair crack prevention effects.

Further, rosemary has cell restoration promotion and lymphatic drainage stimulation effects, has effects on skin aging by promoting generation of fibroblasts, has blood circulation improvement, antibiotic effects, pain killing effects, inflammation improvement, sexual desire reinforcement, and urination stimulation, gives vigor to brain cells by strong fragrance so as to have effects on memory and concentration improvement, dementia prevention and gloss and elastic skin maintenance, and has neuralgia and dandruff treatment effects, hair loss prevention and hair growth stimulation effects.

Further, the tea tree has effects on skin diseases by bacteria, has effects on pimples, eczema, oily skin, athlete's feet, wart, a bite by a bug, dandruff, and injury, and improves the immune system.

Further, cedarwood helps lymphatic drainage, decomposes cellulite, has effects on pimples, oily hair, dandruff and preservation from decay, has urination stimulation effects and sterilization effects so as to have the best effects on oily skin, thereby has pimple treatment effects, seborrhoeic dermatitis treatment effects and hair loss treatment effects, and is used in a hair tonic because of scalp cell detoxication effects.

Step 8 (S800): Maturation in a Warm Temperature for Sufficient Generation of Natural Nutrients In a state in which the mixture including the essential oil is poured in a mould and the mould is shut tight, the mixture is matured at 30 to 40° C. for 48 to 120 hours so as to generate natural nutrients.

The reason why this step is performed in a completely airtight state is because, if the saponificated mixture constantly contacts the air, it becomes hard in a short time. If the mixture becomes hard, the natural nutrients cannot be sufficiently generated, and thus long time maturity in an airtight state in a warm temperature is needed so that natural nutrients and glycerine may be generated.

Step 9 (S900): Maturing Soap in a Room Temperature

After the maturing in a warm temperature, the solid soap is separated from the mould, and is matured in a shady and drafty area in a room temperature of 22 to 28° C. for 4 to 6 weeks.

Through this step, the solid soap is sufficiently dried and matured, and the natural nutrients and glycerine generated in step 8 (S800) are further matured. At this time, if the direct ray of light is thrown on the soap, the color may be changed and the quality may be deteriorated, and thus the soap should be matured in a shady and drafty area.

Step 10 (S1000): Measuring Acidity by pH Test

Some pieces of a natural soap, of which the maturing in a room temperature has been completed, are separated, and a pH test is performed to measure the acidity, and the acidity is checked to confirm whether the acidity is between neutrality and 9 (weak alkali) so as to complete the product.

If the acid soap is used because of insufficient drying, the face turns red and prickles and the skin is injured, and thus the soap is matured in a room temperature for sufficient drying and improvement of the curative effects of the herbal medicine mature decoction, thereby producing high-quality soap.

In the above steps, the following steps may be selectively added.

Optional Step 1 (S650): Adding Functional Powder

This optional step is a step for adding functional powder to the saponificated mixture, and may be optionally added before or after step 7 (S700).

5 to 10% of the functional powder including at least one of black sesame powder, black rice powder, black bean powder, chlorella powder, and Japanese cypress leaf powder may be added to 90 to 95 weight % of the saponificated mixture, and then stirred so as to give functionality to the natural soap.

The black sesame powder has abundant unsaturated fatty acids which prevent hardening of the arteries, vitamin E and phospholipids which restore the skin, lecithin which has positive effects on the brain, supplies nutrition to the scalp so as to prevent hair loss, and has curative effects on constipation.

Further, black rice powder contains vitamin B and vitamin E 4 times greater than those of common rice, thus has excellent effects on prevention of disease of adult people and skin beauty, and has cell activation and aging prevention effects.

Further, the black bean powder normalizes blood pressure, relieves inflammation, and contains vitamin E, unsaturated fatty acids, anthocyanin and beta carotene which prevent aging, and estrogens, saponin and glycinin, etc. which enlarge blood vessels to have effects on white hair and hair loss.

Further, chlorella powder contain special materials which promote growth, and thus disables the power of pollutants, promotes cell division and metabolism, and activates cells so as to have effects on the skin and hair regeneration.

Further, the Japanese cypress leaf powder secretes materials for sterilization which improve body regulation ability, inhibits propagation of germs and fungus, cleans air, prevents and treats allergic diseases, removes unpleasant smell and increases immunity.

Optional Step 2 (S750): Adding Already Produced Natural Soap Fragments of the Present Invention After step 7 (S700), 1 to 15 weight % of the already produced natural soap fragments of the present invention is added to the 85 to 99% of the mixture including the essential oil.

The already produced natural soap fragments of the present invention are added to the mixture including essential oil, and this improves the maturity level, thereby reducing the maturing period and helping to produce highly matured high-quality products.

Maturity level is very important in natural soap manufactured in CP method and herbal medicine contained the soap, and option step 2 has been developed through a lot of experiments with an intention to obtain high quality products by increasing the maturity level.

Experimental Example 1

Experiment of Efficacy of Natural Soap of the Embodiment of the Present Invention Through the embodiment of the present invention, natural soap using the herbal medicine mature decoction is produced, and the efficacy of the soap is experimented by making men and women in their 30s to 60s use the soap for more than 1 month (30 days).

As shown in FIG. 2, "questionnaire after use of the product" is distributed, and the subjects evaluate the soap and record their evaluation according to the criteria disclosed in the questionnaire (Very good (5), Good (4), Not bad (3), Bad (2), Very bad (1)), and the result is shown in Table 1 below.

TABLE 1

| Evaluation Item | 30s | 40s | 50s | 60s | Average |
|---|---|---|---|---|---|
| (Men) | | | | | |
| Hair loss prevention | 5 | 5 | 5 | 5 | 5 |
| Hair growth stimulation | 5 | 5 | 5 | 5 | 5 |
| Soap bubbles | 5 | 5 | 5 | 4.5 | 4.9 |
| Detergency | 5 | 5 | 5 | 5 | 5 |
| Fragrance | 3.7 | 4.3 | 4.4 | 3.5 | 4 |
| Moisturizing effect | 5 | 5 | 4.8 | 4.5 | 4.8 |
| (Women) | | | | | |
| Hair loss prevention | 5 | 5 | 5 | 4.8 | 5 |
| Hair growth stimulation | 4.5 | 5 | 4.5 | 4.7 | 4.7 |
| Soap bubbles | 5 | 5 | 5 | 4.7 | 4.9 |
| Detergency | 5 | 5 | 5 | 5 | 5 |
| Fragrance | 4 | 4.5 | 4 | 3.8 | 4 |
| Moisturizing effect | 5 | 5 | 5 | 5 | 5 |

Referring to Table 1 above, most of men and women in 30s to 60s have marked "very good" for hair loss prevention, hair growth stimulation, soap bubbles, detergency and moisturizing effect, and marked "good" only for fragrance. This is because most of people including the subjects of this experiment have used products containing artificial fragrance. Because natural fragrance is weak, artificial fragrance has been added, but it may be harmful to the human body.

This may be resolved by adjusting the amount of essential oil.

Referring to the comments of some of the subjects of this experiment, Ms. Lee, one woman in her 30s, said "I was suffering from serious hair loss, keratin, and the itching, but all of these problems have been improved since I used this soap . . . " Ms. Park in her 60s said "my hair was weak and hair loss was severe after dyeing and perm. However, as I used natural soap, hair loss has been improved, hair became stronger, dandruff has been improved, and hair has been moisturized. This is really a good functional product for hair growth stimulation." Ms. Yang in her 60s said, "I found a lot of hairs on the floor whenever I cleaned the bathroom. However, after I used the natural soap for 30 days, hair loss stopped, and hair growth has been stimulated." Ms. Jeong in his 40s said, "I received this soap as a gift from one of my friends. After I used this, hair loss was stopped, and hair growth has been started. Thank you." Likewise, many people's comments are proving the efficacy of the natural soap of the present invention.

In this way, a natural soap made of herbal medicines having excellent effects of hair loss prevention and hair growth stimulation has been developed, and according to the present invention, it has become possible to provide a natural soap using a herbal medicine mature decoction which may be easy to be used by significantly reducing unpleasant smell of natural herbs, may be mixed with various natural herbs by reducing the attribute of the natural herbs of being separated from an carrier oil, may be stored for a long time by doubling elements having medical effects of natural herbs, may prevent loss of hair and stimulate hair growth by improving detergency using grain powder without using a synthetic surfactant, and a method of preparing the same.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A natural soap made using a herbal medicine mature decoction, comprising herbs including lotus roots, lotus leaves, red ginseng, *Hippophae rhamnoides* leaves and trunk, persimmon leaves, *thuja orientalis*, ginger, rosemary, black beans, black sesame, aloe, mulberry leaves, *Orostachys japonicus, Angelica gigas*, green tea, pine needles, mint, *pleuropterus multiflorus*, blueberry, and *Acorus gramineus*,
   wherein a ripening device ripens the herbs in temperatures of 65 to 95° C. for 3 to 15 days,
   wherein distilled water or soft water is poured onto the herbs, and
   wherein the herbs mixed with the water are decocted by a decoction maker.

2. The natural soap of claim 1, wherein the herbal medicine decoction is obtained by ripening the herbs in the temperatures along with the distilled water or soft water in the decoction maker, then boiling the herbs mixed with the water by heat, then decocting the herbs mixed with the water by the heat so as to make a first decoction, then pouring the first decoction into another vessel, then pouring the distilled water or soft water in the decoction maker, then boiling the herbs mixed with the water by the heat, then decoct the herbs mixed with the water by the heat so as to make a second decoction, then removing the herbs from the second decoction, then mixing the first decoction with the second decoction, and then decocting the mixed decoction by the heat.

3. A method of preparing a natural soap by adding a caustic soda, the method comprising:
   washing herbs including 6 to 9 weight % of lotus roots, 4 to 6 weight % of lotus leaves, 4 to 6 weight % of red ginseng, 4 to 6 weight % of *Hippophae rhamnoides* leaves and trunk, 4 to 6 weight % of persimmon leaves, 4 to 6 weight % of *thuja orientalis*, 4 to 6 weight % of ginger, 3 to 5 weight % of rosemary, 6 to 9 weight % of black beans, 3 to 5 weight % of black sesame, 5 to 8 weight % of aloe, 5 to 8 weight % of mulberry leaves, 1 to 3 weight % of *Orostachys japonicus*, 4 to 6 weight % of *Angelica gigas*, 3 to 5 weight % of green tea, 5 to 8 weight % of pine needles, 4 to 6 weight % of mint, 4 to 6 weight % of *pleuropterus multiflorus*, 3 to 5 weight % of blueberry, and 3 to 5 weight % of *Acorus gramineus*, putting the washed herbs in a ripening device, and ripening the herbs at temperatures of 65 to 95° C. for 3 to 15 days (S100);

putting the ripened herbs along with 15 to 25 weight % of distilled water and 75 to 85 weight % of soft water in a decoction maker, boiling the herbs and mixing the herbs with the water by heat, and decocting the herbs mixed with the water by the heat for 48 to 72 hours so as to make a first decoction (S200);

pouring the first decoction into a vessel, putting 37 to 43 weight % of distilled water or soft water in the decoction maker, boiling the herbs mixed with the water by the heat and decocting the herbs and mixing the herbs with the water by the heat for 3 to 4 hours so as to make a second decoction (S300);

removing the herbs from the decoction maker, mixing the first decoction with the second decoction, and decocting the mixed decoction for 24 to 36 hours by the heat so as to obtain an herbal medicine decoction of 7.5 to 8.5 weight % (S400);

mixing 65 to 75 weight % of the herbal medicine decoction with 25 to 35 weight % of the caustic soda, and cooling the mixture down to temperature of 40 to 55° C. (S500);

heating carrier oil, which is a mixture of at least two of coconut oil, palm oil, olive oil, camellia oil, castor oil, rice bran oil, sunflower oil, and grape seed oil, to 40 to 55° C., and pouring 25 to 35 weight % of the cooled mixture of the caustic soda and the herbal medicine decoction into 65 to 75 weight % of the heated carrier oil and stirring the mixture to form a soap (S600);

adding 2 to 5 weight % of essential oil, which is a mixture of at least two of lavender, lemon, clary sage, ylang ylang, rosemary, tea tree, and cedarwood, to 95 to 98 weight % of saponified mixture, and stirring the mixture (S700);

pouring the mixture including the essential oil into a mould, and maturing the mixture at temperature of 30 to 40° C. for 48 to 72 hours (S800); and separating a solid soap from the mould after the maturing of the mixture, and maturing the soap in a shady area in a room temperature of 22 to 28° C. for to 6 weeks (S900).

4. The method of claim 3, further comprising:

adding 5 to 10% of a powder including at least one of black sesame powder, black rice powder, black bean powder, chlorella powder, and Japanese cypress leaf powder to 90 to 95 weight % of the saponified mixture, and stirring the mixture (S650).

5. The method of claim 3, further comprising:

adding 85 to 99 weight % of the saponified mixture having the essential oil to 1 to 15 weight % of fragments of the natural soap (S750).

* * * * *